United States Patent
Nishimura et al.

(10) Patent No.: US 6,852,735 B1
(45) Date of Patent: Feb. 8, 2005

(54) SIASTATIN B DERIVATIVES HAVING A GLYCOSIDASE INHIBITORY ACTIVITY AND PROCESSES FOR PRODUCING THE SAME

(75) Inventors: Yoshio Nishimura, Komae (JP); Eiki Shitara, Yokohama (JP); Tomio Takeuchi, Tokyo (JP)

(73) Assignees: Zaidan Hojin Biseibutsu Kagaku Kenkyu Kai, Tokyo (JP); Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/868,780

(22) PCT Filed: Dec. 24, 1999

(86) PCT No.: PCT/JP99/07269

§ 371 (c)(1),
(2), (4) Date: Jun. 21, 2001

(87) PCT Pub. No.: WO00/39140

PCT Pub. Date: Jul. 6, 2000

(30) Foreign Application Priority Data

Dec. 25, 1998 (JP) .................................... 10-370277

(51) Int. Cl.[7] .................. A61K 31/445; C07D 211/36; C07D 211/60
(52) U.S. Cl. .................. 514/315; 546/242; 546/245
(58) Field of Search ................. 546/242, 245; 514/315

(56) References Cited

PUBLICATIONS

Nishmura et al J. Am. Chem. Soc. vol. 110, pp 7249–7250 (1988).*
Jensen et al, "Synthesis and investigation of L–fuco– and D–glucurono–azafagomie" J. Chem. Soc. Perkins 1, vol. 1, No. 9 (2002.*
Nishmura et al, Jol. of Antibiotics, vol. 45, No. 6, pp. 963–970.*
Kudo et al, Jol. of Antibiotics, vol. 45, No. 6, pp. 963–970.*

* cited by examiner

Primary Examiner—Cecilia Tsang
Assistant Examiner—Raymond Covington

(74) Attorney, Agent, or Firm—Stites & Harbison PLLC; B. Aaron Schulman

(57) ABSTRACT

A compound of the formula (I):

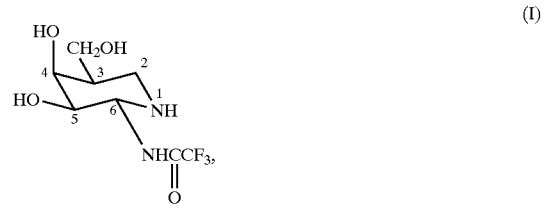

and a compound of the formula (V):

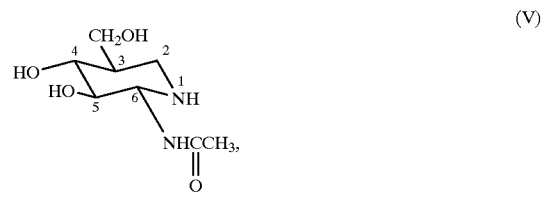

as well as a compound of the formula (X):

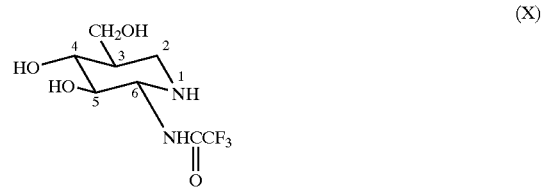

which are each a novel siastatin B derivative having a potent inhibitory activity against a glycosidase, are now synthesized by new processes.

The compound of the formula (I), the compound of the formula (V) and the compound of the formula (X) have a potent enzyme-inhibitory activity to a glycosidase, which is particularly N-acetyl-galactosaminidase, galactosidase, glucosidase and mannosidase.

8 Claims, No Drawings

SIASTATIN B DERIVATIVES HAVING A GLYCOSIDASE INHIBITORY ACTIVITY AND PROCESSES FOR PRODUCING THE SAME

TECHNICAL FIELD

This invention relates to novel siastatin B derivatives each having an activity inhibitory to a glycosidase, and their pharmaceutically acceptable salts. Particularly, this invention relates to 6-deacetamido-3-decarboxy-3-hydroxymethyl-6-trifluoroacetamido-siastatin B and its 4-epi isomer as well as 3-decarboxy-4-epi-3-hydroxymethyl-siastatin B, which are said novel siastatin B derivatives, or their pharmaceutically acceptable salts. Moreover, this invention relates to processes for producing such novel siastatin B derivatives. Furthermore, this invention also relates to a pharmaceutical composition which comprises as an active ingredient said novel siastatin B derivative, as well as to a glycosidase inhibitor.

BACKGROUND ART

Various glycosidases are known as an enzyme which is widely distributed in animal cells, microorganisms, viruses, etc. In mammalian animals, it has been considered that glycosidases control a great variety of physiological mechanisms, including canceration of normal cells, metastasis of cancer cells, viral or bacterial infection, immunological functions, fertilization of an ovum, and others in which glycoproteins and glycolipid-glycosyl chains participate through the carbohydrate metabolism. Moreover, certain glycosidases participate in the digestive mechanism of food through the degradation of polysaccharides such as starch, sucrose, and oligosaccharides etc. Furthermore, it has been found that a substance inhibitory to a glycosidase which can liberate the glycosyl chains as combined in a cell membrane is possible to have an immunomodulating action and an action which controls the metastasis of cancer cells, as well as an action which controls infection of an AIDS virus or an influenza virus. Moreover, substances inhibitory to a glycosidase having catabolism which participates in the digestive mechanism of food are found to be important, since they are useful as an antidiabetic agent or an antiobestic agent.

Thus, in view that a glycosidase is an enzyme which is important in the living body, it is also important to study physiological properties of a glycosidase. In the study of the properties of a glycosidase, use can be made of such a substance having an action which inhibits the enzymatic activity of a glycosidase. Moreover, it can be expected that certain glycosidase-inhibitory substances can be utilized as an inhibitor to the metastasis of cancer cells. Therefore, it has been keenly demanded to provide such a novel compound which is of low toxicity, which is water-soluble and which has a potent glycosidase-inhibitory activity.

It is an object of this invention to provide a novel siastatin B derivative which exhibits a potent activity inhibitory to a glycosidase. Moreover, it is another object of this invention to provide processes for producing such a new siastatin B derivative.

It are still another objects to provide a pharmaceutical composition comprising as an active ingredient said siastatin B derivative having the glycosidase-inhibitory activity, and also to provide a glycosidase inhibitor consisting of said siastatin B derivative.

DISCLOSURE OF INVENTION

In order to achieve the above-mentioned objects of this invention, we, the present inventors, have paid attention to a siastatin B derivative active as a glycosidase inhibitor, and have synthesized many siastatin B derivatives, and eagerly have made research about the biological activities of these siastatin B derivatives. As a result, the present inventors have now succeeded in synthesizing three new siastatin B derivatives which each have a potent glycosidase-inhibitory activity and are represented by the formulae (I), (V) and (X) given hereinafter, respectively. Moreover, the present inventors have now devised new production processes which are able to synthesize effectively the new siastatin B derivatives of the formulae (I), (V) and (X). Based on these findings, the present inventions have completed this invention.

According to the first aspect of this invention, therefore, there is provided 6-deacetamido-3-decarboxy-3-hydroxymethyl-6-trifluoroacetamido-siastain B represented by the formula (I):

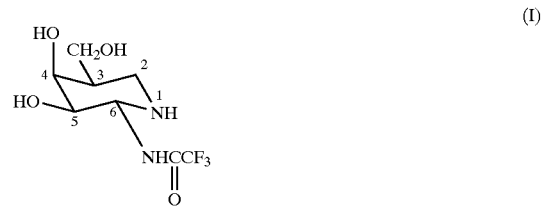

or a pharmaceutically acceptable salt thereof.

According to the second aspect of this invention, there is provided 3-decarboxy-4-epi-3-hydroxymethyl-siastain B represented by the formula (V):

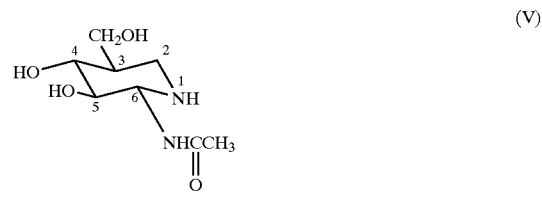

or a pharmaceutically acceptable salt thereof.

According to the third aspect of this invention, there is provided 6-deacetamido-3-decarboxy-4-epi-3-hydroxymethyl-6-trifluoroacetamido-siastain B represented by the formula (X):

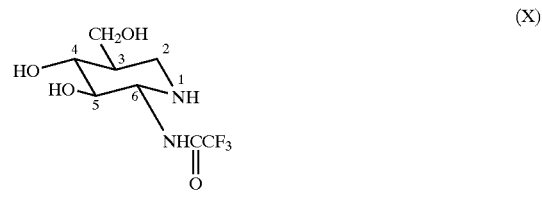

or a pharmaceutically acceptable salt thereof.

The salts of the siastatin B derivatives having the formulae (I), (V) and (X), which are provided respectively according to the first aspect, the second aspect and the third aspect of this invention, include acid addition salts at the imino group of the compounds of these formulae. Such acid addition salts include in particular such pharmaceutically acceptable acid addition salts of said compounds with a pharmaceutically acceptable inorganic acid such as hydrochloric acid and sulfuric acid, or a pharmaceutically acceptable organic acid such as acetic acid, propionic acid, etc.

Next, described are the physicochemical properties of the hydrochloride (i.e. hydrochloric acid addition salt) of each of 6-deacetamido-3-decarboxy-3-hydroxymethyl-6-trifluoroacetamido-siastain B of the formula (I), 3-decarboxy-4-epi-3-hydroxymethyl-siastain B of the formula (V) and 6-deacetamido-3-decarboxy-4-epi-3-hydroxymethyl-6-trifluoroacetamido-siastain B of the formula (X) which are provided respectively according to the first aspect, the second aspect and the third aspect of this invention.

(1) 6-Deacetamido-3-decarboxy-3-hydroxymethyl-6-trifluoroacetamido-siastain B [the compound of the formula (I)]

Color and Appearance: Colorless amorphous solid;
Molecular formula: $C_8H_{13}N_2O_4F_3 \cdot HCl$;
Specific rotation: $[\alpha]^{27}_D +38.8°$ (c 0.64, methanol);
$^1$H-NMR spectrum ($CD_3OD$, δ ppm): 2.06–2.15(1H, m, 5-H), 3.18(1H, br t, J=12.0 Hz, 6-Hax), 3.22(1H, dd, J=12.3, 5.4 Hz, 6-Heq), 3.58(1H, dd, J=10.7, 7.3 Hz, —$CH_2OH$), 3.69(1H, dd, J=10.7, 6.4 Hz, —$CH_2OH$), 3.90(1H, dd, J=10.3, 2.9 Hz, 3-H), 4.08–4.12(1H, m, 4-H), 5.07(1H, d, J=10.3 Hz, 2-H);
IR spectrum (KBr): 3300, 2890, 1720, 1550, 1430, 1220, 1180 $cm^{-1}$;
Mass spectrum (FAB-MS): m/z 259.2(M+H)$^+$, 185.2, 146.2, 93.1, 75.1, 57.1;

(2) 3-Decarboxy-4-epi-3-hydroxymethyl-siastain B [the compound of the formula (V)]

Color and Appearance: Colorless amorphous solid;
Molecular formula: $C_8H_{16}N_2O_4 \cdot HCl$;
Specific rotation: $[\alpha]^{26}_D +45.4°$ (c 0.50, methanol);
$^1$H-NMR spectrum ($CD_3OD$, δ ppm): 1.83–1.97(1H, m, 5-H), 2.06(1H, s, —$NHCOCH_3$), 3.04(1H, br t, J=12.7 Hz, 6-Hax), 3.36(1H, dd, J=13.2, 4.4 Hz, 6-Heq), 3.47(1H, dd, J=10.8, 8.8 Hz, 4-H), 3.60(1H, dd, J=10.3, 8.8 Hz, 3-H), 3.65(1H, dd, J=11.2, 6.8 Hz, —$CH_2OH$), 3.83(1H, dd, J=11.2, 3.4 Hz, —$CH_2OH$), 4.71(1H,d, J=10.3 Hz, 2-H);
IR spectrum (KBr): 3350, 1680, 1550, 1380, 1290, 1100, 1060, 890 $cm^{-1}$;
Mass spectrum (FAB-MS): m/z 205.2 (M+H)$^+$, 154.1, 146.1, 136.1, 107, 89, 77;

(3) 6-Deacetamido-3-decarboxy-4-epi-3-hydroxymethyl-6-trifluoroacetamido-siastain B [the compound of the formula (X)]

Color and Appearance: Colorless amorphous solid;
Molecular formula: $C_8H_{13}N_2O_4F_3 \cdot HCl$;
Specific rotation: $[\alpha]^{26}_D +35.0°$ (c 0.50, methanol);
$^1$H-NMR spectrum ($CD_3OD$, δ ppm): 1.88–2.00(1H, m, 5-H), 3.11(1H, br t, J=13.2 Hz, 6-Hax), 3.42(1H, dd, J=13.2, 4.4 Hz, 6-Heq), 3.51(1H, dd, J=10.3, 9.3 Hz, 4-H), 3.67(1H, dd, J=11.2, 6.4 Hz, —$CH_2OH$), 3.73(1H, dd, J=10.3, 8.8 Hz, 3-H), 3.84(1H, dd, J=11.2, 3.9 Hz, —$CH_2OH$), 4.84(1H, d, J=9.8 Hz, 2-H);
IR spectrum (KBr): 3350, 1740, 1570, 1420, 1230, 1180, 1100, 1060, 990, 880 $cm^{-1}$;
Mass spectrum (FAB-MS): m/z 259.1 (M+H)$^+$, 202.2, 154.1, 146.1, 136.1, 128.1, 107, 77.1, 57.1.

The following Test Examples 1 to 5 given below demonstrate that each of 6-deacetamido-3-decarboxy-3-hydroxy-methyl-6-trifluoroacetamido-siastain B of the formula (I), 3-decarboxy-4-epi-3-hydroxymethyl-siastain B of the formula (V) and 6-deacetamido-3-decarboxy-4-epi-3-hydroxymethyl-6-trifluoroacetamido-siastain B of the formula (X) according to this invention have the glycosidase-inhibitory activity.

TEST EXAMPLE 1

This Test Example is a test example for determining the N-acetylgalactosaminidase-inhibitory activity of the compound of the formula (I), (V) or (X) according to this invention.

Assay of the N-acetylgalactosaminidase-inhibitory activity was conducted according to a modification of the method described in the "Journal of Biological Chemistry", 252, pp.5194–5200(1977).

Thus, 0.5 mL of 0.025M citrate-phosphate buffer (pH 4.0), 0.1 mL of the same buffer containing 10 mM p-nitrophenyl-N-acetyl-α-D-galactosaminide dissolved therein, and 0.1 mL of either water or an aqueous solution containing as the test compound any one of the compounds of the formulae (I), (V) and (X) according to this invention were mixed with each other and pre-incubated in a 96-wells titer plate at 37° C. for 10 minutes. After the completion of the pre-incubation, to the pre-incubated mixture was added 0.01 mL of 0.025 M citrate-phosphate buffer containing α-N-acetyl-galactosaminidase originated from chicken liver (a product of Sigma Company) which was dissolved in said buffer as a glycosidase to be tested. Thereafter, the enzymatic reaction was conducted at 37° C. for 30 minutes.

After the enzymatic reaction, to the reaction solution was added 1.0 mL of 0.3M glycine—sodium hydroxide buffer (pH 10.5), in order to terminate the enzymatic reaction. Thereafter, the absorbance [designated as value (a)] of light at 405 nm of the resulting reaction solution was measured. Concurrently, measurement was made of the absorbance [designated as value (b)] at 405 nm of the reaction solution as obtained in the control test where the enzymatic reaction was conducted without addition of the test compound. Further, measurements were made of the absorbance [designated as values (a')] and the absorbance [[designated as values (b')] at 405 nm of the solutions as obtained in the blank test and the control test, respectively, where the enzymatic reaction was not conducted in the assay test. The rate of inhibition to N-acetylglucosaminidase was calculated by the equation:

$$[1-(a-a')/(b-b')] \times 100.$$

The concentration at which the test compound inhibits by 50% the activity of the enzyme tested, namely the concentration of the test compound capable of exhibiting 50% inhibition to the enzyme was estimated as the value of $IC_{50}$. The test results obtained are summarized as $IC_{50}$ value in Table 1 below.

TEST EXAMPLE 2

This Test Example is a test example for determining the N-acetylglucosaminidase-inhibitory activity of the compound of the formula (I), (V) or (X) according to this invention.

The evaluation of the N-acetylglucosaminidase-inhibitory activity was conducted according to a modification of the method described in the "Methods in Enzymology", 28, p.772 (1972).

Namely, the test was conducted in the same manner as the test for the N-acetylgalactosamnidase-inhibitory activity as described above, but with using β-N-acetyl-galactosaminidase (a product of Sigma Company) originated from bovine epididymis, as the glycosidase enzyme to be tested, and with using p-nitrophenyl-N-acetyl-β-D-glucosaminide as the substrate. Furthermore, absorbances of light at 405 nm were measured in the same manner as described in Test Example 2 above. $IC_{50}$ value of the test compound capable of giving the 50% inhibition to β-N-acetyl-glucosaminidase was calculated. The $IC_{50}$ value is shown in Table 1 given below.

TEST EXAMPLE 3

This Test Example is a test example for determining the α-galactosidase or β-galactosidase-inhibitory activity of the compound of the formula (I), (V) or (X) according to this invention.

The evaluation of the α-galactosidase or β-galactosidase-inhibitory activity was conducted according to a modification of the method described in the "Journal of Biological Chemistry", 240, p.2468 (1965).

Namely, the test was conducted in the same manner as the test for the enzyme-inhibitory activity described in Test Example 1, but with using α-galactosidase or β-galactosidase (products of by Sigma Company) originated from *Aspergillus niger*, as the glycosidase enzyme, and with using p-nitrophenyl-α-D-galactoside and p-nitrophenyl-β-D-galactoside as the substrate. Furthermore, absorbances of light at 405 nm were measured in the same manner as in Test Example 1. $IC_{50}$ values of the test compound capable of giving the 50% inhibition to the enzymes were calculated. The $IC_{50}$ values are shown in Table 1 given below.

Namely, the test was conducted in the same manner as the test for the enzyme-inhibitory activity test described in Test Example 1, but with using α-mannosidase from jack bean or β-mannosidase from snail (both enzymes are products of Sigma Company) as the glycosidase enzyme, with using 0.05 M sodium acetate—acetate buffer (pH 4.5) as the buffer, and with using p-nitrophenyl-α-D-mannoside or p-nitrophenyl-β-D-mannoside as the substrate. Furthermore, absorbances of light were measured in the same manner as in Test Example 1. $IC_{50}$ values of the test compound capable of giving the 50% inhibition to the enzymes were calculated. The $IC_{50}$ values are shown in Table 1 giving below.

TABLE 1

| Compound of the invention | 50% inhibiory concentration ($IC_{50}$) (μg/ml) | | | | | | | |
| --- | --- | --- | --- | --- | --- | --- | --- | --- |
| | Enzyme $A^a$ | Enzyme $B^b$ | Enzyme $C^c$ | Enzyme $D^d$ | Enzyme $E^e$ | Enzyme $F^f$ | Enzyme $G^g$ | Enzyme $H^h$ |
| Formula (I) | 0.65 | 22 | 0.1 | 0.05 | 0.14 | 38 | >100 | >100 |
| Formula (V) | >100 | 3 | >100 | >100 | 1.4 | 10 | 65 | 7 |
| Formula (X) | >100 | >100 | >100 | 60 | 0.13 | 1 | 0.75 | 0.06 |

(Note):
[a]Enzyme A: α-N-acetylgalactosaminidase (from chicken liver)
[b]Enzyme B: β-N-acetylglucosaminidase (from bovine epididymis)
[c]Enzyme C: α-D-galactosidase (from *Aspergillus niger*)
[d]Enzyme D: β-D-galactosidase (from *Aspergillus niger*)
[e]Enzyme E: β-D-glucosidase (from almond)
[f]Enzyme F: β-D-mannosidase (from snail)
[g]Enzyme G: α-D-mannosidase (from jack bean)
[h]Enzyme H: α-D-glucosidase (from yeast)

TEST EXAMPLE 4

This Test Example is a test example for determining the α-glucosidase or β-glucosidase-inhibitory activity of the compound of the formula (I), (V) or (X) according to this invention.

The evaluation of the β-glucosidase-inhibitory activity was conducted according to a modification of the method described in the "Agricultural and Biological Chemistry", 26, p.203 (1962).

Namely, the test was conducted in the same manner as the test for the enzyme-inhibitory activity described in Test Example 1, but with using α-glucosidase originated from yeast or β-glucosidase originated from almond (both enzymes are products of Sigma Company) as the glycosidase enzyme, and with using p-nitro-phenyl-α-D-glucoside or p-nitrophenyl-β-D-glucoside as the substrate. Furthermore, absorbances of light were measured in the same manner as in Test Example 1, and $IC_{50}$ values of the test compound capable of giving the 50% inhibition to the enzyme were calculated. The $IC_{50}$ values are shown in Table 1 giving below.

TEST EXAMPLE 5

This Test Example is a test example for determining the α-mannosidase or β-mannosidase-inhibitory activity of the compounds according to this invention.

The evaluation of the β-mannosidase-inhibitory activity was conducted according to a modification of the method described in the "Journal of Biological Chemistry", 242, p.5474 (1967).

As shown in Table 1, the compound of the formula (I) according to the first invention is able to inhibit strongly N-acetylglucosaminidase, N-acetyl-galactosaminidase, α-D-galactosidase, β-D-galactosidase, β-D-glucosidase and β-D-mannosidase. Moreover, the compound of the formula (V) according to the second invention is able to inhibit strongly β-N-acetylglucosaminidase, β-D-mannosidase, β-D-glucosidase, α-D-mannosidase and α-D-glucosidase. Furthermore, the compound of the formula (X) according to the third invention is able to inhibit strongly β-D-galactosidase, β-D-mannosidase, β-D-glucosidase, α-D-mannosidase and α-D-glucosidase. Therefore, the new compounds according to these inventions are significantly effective as the inhibitor to said enzymes.

Moreover, it can be presumed that the compounds having the formulae (I), (V) and (X) respectively according to this invention have not only an activity to inhibit a glycosidase which participates in the mechanism of metastasis of the cancer cells in mammalian animals and the mechanism of infection of an AIDS virus, but also an activity to inhibit a glycosidase having catabolism which participates in the digestive mechanism of food. In this view, these new compounds of this invention can be expected to be useful as such an inhibitor to metastasis of cancer cells, which can be used for the treatment of cancer, and as an inhibitor to infection of an AIDS virus and as an antidiabetic or an antiobestic agent. Moreover, these new compounds of this invention are useful as a reagent for studying the function of a glycosidase in the living body.

Next, described is the process for producing 6-deacetamido-3-decarboxy-3-hydroxymethyl-6-trifluoroacetamido-siastatin B of the formula (I).

In the production of 6-deacetamido-3-decarboxy-3-hydroxymethyl-6-trifluoroacetamido-siastain B of the formula (I) according to the first aspect of this invention, there is used as the first starting material, an N-protected or unprotected-4,5-O-protected-3-hydroxymethyl-3-decarboxy-siastatin B represented by the general formula (II):

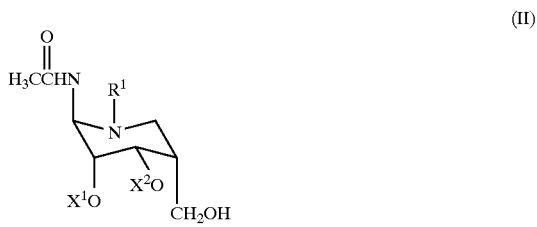

(II)

wherein $R^1$ is a hydrogen atom or an imino-protecting group, $X^1$ and $X^2$ each are a monovalent hydroxyl-protecting group, or both $X^1$ and $X^2$ together denote a divalent hydroxyl-protecting group. This compound of the formula (II) can be produced from siastatin B (Japanese Patent Publication "Kokoku" No. Sho 55-46714) which is obtained by cultivating *Streptomyses verticillus* var. *quintum* (FERM P-507) which is an actinomyces, according to the method described in Japanese Patent Prepublication "Kokai" No. Hei 9-157254 or the method of Sato et al as described in the "Carbohydrate Research", 286, p.173–178 (1966).

The imino-protecting group ($R^1$) in the compound of the formula (II) may preferably be an alkoxycarbony group, an aryloxycarbonyl group or an aralkyloxycarbonyl group, which can be eliminated by a hydrolysis method. Especially, tert-butoxycarbonyl group is convenient.

Introduction of the imino-protecting group ($R^1$) can be carried out by conventional procedures. The divalent hydroxyl-protecting group (formed by combining $X^1$ and $X^2$ together) which protects simultaneously the two hydroxyl groups at 4-position and 5-position of the compound of the formula (II) may conveniently be benzylidene group. However, in general, another various divalent hydroxyl-protecting groups can be employed as the hydroxy-protecting groups $X^1$ and $X^2$. Namely, there can be employed a divalent hydroxyl-protecting group represented by the formula

wherein Y and Z may be the same or different from each other, and are individually hydrogen, an alkyl group (preferably, a lower alkyl group of 1 to 4 carbon atoms) or an aryl group (preferably, phenyl group or a substituted phenyl group, for example, p-methoxyphenyl group). For example, instead of benzylidene group, isopropylidene group or a cycloalkylidene group such as cyclohexylidene group, or tetrahydropyranylidene group can be also employed to protect the two hydroxyl groups at 4-position and 5-postion of the compound of the formula (II).

The introduction of such divalent hydroxyl-protecting group may be conducted according to conventional method for production of hydroxyl group which has been employed in sugar chemistry for protecting simultaneously such two hydroxyl groups as bounded to two adjacent carbon atoms. Alternatively, as suitable monovalent hydroxyl-protecting group ($X^1$ and $X^2$), a trialkylsilyl group, especially tert- butyldimethylsilyl group can be used and introduced according to conventional procedures. The compound of the formula (II) prepared as described above is employed as the starting compound and may be converted chemically in a plural of steps, so that 6-deacetamido-3-decarboxy-3-hydroxymethyl-6-trifluoroacetamido-siastatin B of the formula (I) can be produced.

Therefore, according to the fourth aspect of this invention, there is provided a process for the production of 6-deacetamido-3-decarboxy-3-hydroxymethyl-6-trifluoro-acetamido-siastain B represented by the formula (I):

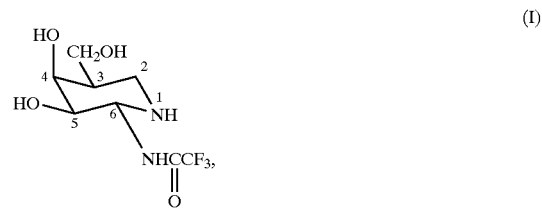

(I)

characterized in that the process comprises:

eliminating the N-acetyl group from an N-protected or unprotected-4,5-O-protected-3-hydroxymethyl-3-decarboxy-siastatin B represented by the general formula (II):

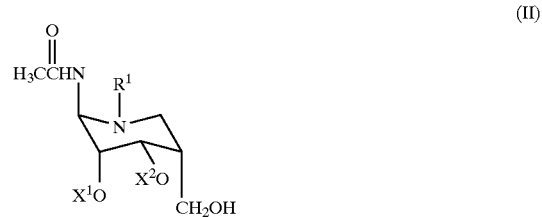

(II)

wherein $R_1$ is a hydrogen atom or an imino-protecting group, $X^1$ and $X^2$ each are a monovalent hydroxyl-protecting group, or both $X^1$ and $X^2$ together denote a divalent hydroxyl-protecting group, to produce an N-protected or unprotected-4,5-O-protected-3-hydroxymethyl-de-N-acetyl-3-decarboxy-siastatin B represented by the general formula (III):

(III)

wherein $R^1$, $X^1$ and $X^2$ have the same meanings as above;

trifluoroacetylating the free amino group of the compound of the formula (III), to produce an N-protected or unprotected-4,5-O-protected-6-deacetamido-3-hydroxymethyl-6-trifluoroacetamido-3-decarboxy-siastatin B represented by the general formula (IV):

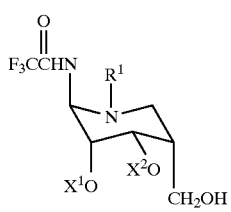

(IV)

wherein $R^1$, $X^1$ and $X^2$ have the same meanings as above;

and then eliminating the imino-protecting group ($R^1$) if present, and eliminating the hydroxyl-protecting groups ($X^1$ and $X^2$) from the compound of the formula (IV).

In carrying out the above process according to the fourth aspect of this invention, first of all, an N-protected or unprotected-4,5-O-protected-3-hydroxymethyl-3-decarboxy-siastatin B of the formula (II) is dissolved in a solvent such as methanol or is used without a solvent, and to this compound of the formula (II) was added hydrazine and then hydrazinolysis is effected at room temperature. Thereby, N-acetyl group of the compound of the formula (II) is eliminated to generate the free amino group, and thus an N-protected or unprotected-4,5-O-protected-6-N-deacetyl-3-hydroxymethyl-3-decarboxy-siastatin B of the formula (III) is produced.

Then, the compound of the formula (III) is allowed to react with ethyl trifluoroacetate in the presence of a base such as N,N'-diisopropylethylamine in a solvent such as N,N'-dimethylformamide, or is allowed to react with trifluoroacetic anhydride in the presence of a base such as pyridine in a solvent such as methylene chloride. Thereby, the free amino group of the compound of the formula (III) is trifluoroacetylated to produce an N-protected or unprotected-4,5-O-protected-6-deacetamido-3-hydroxymethyl-6-trifluoro-acetamido-siastatin B of the formula (IV). Furthermore, the protecting groups ($R^1$, $X^1$ and $X^2$) are eliminated from the compound of the formula (IV) according to conventional procedures, whereby the aimed 6-deacetamido-3-decarboxy-3-hydroxymethyl-6-trifluoroacetamido-siastain B represented of the formula (I) is produced.

Furthermore, when the imino-protecting group ($R^1$) and hydroxyl-protecting groups ($X^1$ and $X^2$) are to be eliminated from the compound of the formula (IV), such elimination reaction may be performed by the suitable method such as hydrolysis or hydrogenolysis, depending on the kind of the protecting groups. For example, when the imino-protecting group ($R^1$) is tert-butoxycarbony group (Boc), the compound of the formula (IV) as mentioned above is dissolved in an organic solvent containing hydrogen chloride, such as 1 to 4 N hydrochloric acid—dioxane, and the resulting solution is allowed to stand at room temperature for 1 to 12 hours, whereby the imino-protecting group, Boc can be removed. Besides, when the hydroxyl-protecting groups ($X^1$ and $X^2$) are benzylidene group, such benzylidene group can be removed by hydrogenolysis in the presence of 10% palladium on carbon under atmosphere of hydrogen.

Next, a process for producing 3-decarboxy-4-epi-3-hydroxymethyl-siastain B of the formula (V) according to the second aspect of this invention is described below.

In the production of 3-decarboxy-4-epi-3-hydroxymethyl-siastain B of the formula (V) according to the second aspect of this invention, there is used as the first starting material an N-protected or unprotected-4,5-O-protected-3-hydroxymethyl-3-decarboxy-siastatin B of the general formula (II) as described above, similarly to the process according to the fourth aspect of this invention.

The compound of the formula (II) is used as the starting compound and is to converted chemically in a plural of steps, so that 3-decarboxy-4-epi-3-hydroxymethyl-siastain B of the formula (V) can be produced.

Namely, according to the fifth aspect of this invention, there is provided a process for the production of 3-decarboxy-4-epi-3-hydroxymethyl-siastain B represented by the formula (V):

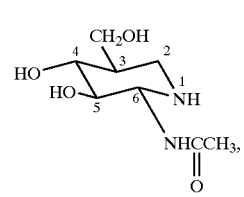

(V)

characterized in that the process comprises:

eliminating the hydroxyl-protecting groups ($X^1$ and $X^2$) from an N-protected or unprotected-4,5-O-protected-3-hydroxymethyl-3-decarboxy-siastatin B represented by the formula (II):

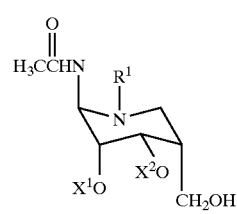

(II)

wherein $R^1$ is a hydrogen atom or an imino-protecting group, and $X^1$ and $X^2$ each are a monovalent hydroxyl-protecting group, or both $X^1$ and $X^2$ together denote a divalent hydroxyl-protecting group, to produce an N-protected or unprotected-3-hydroxymethyl-3-decarboxy-siastatin B represented by the general formula (VI):

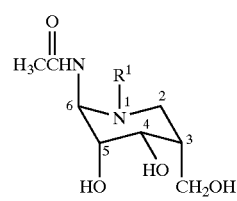

(VI)

wherein $R^1$ has the same meanings as above;

protecting both of the hydroxyl group at 3-position and the free hydroxyl group at 5-position of the compound of the formula (VI), to produce an N-protected or unprotected-5-O-protected-3-protected hydroxymethyl-3-decarboxy-siastatin B represented by the general formula (VII):

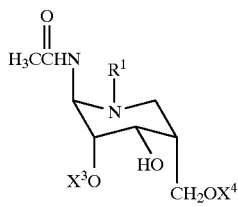

(VII)

wherein $R^1$ is a hydrogen atom or an imino-protecting group, $X^3$ and $X^4$ each denote a hydroxyl-protecting group;

oxidizing the hydroxyl group at 4-position of the compound of the formula (VII), to produce an N-protected or unprotected-4-keto-5-O-protected-3-protected hydroxymethyl-3-decarboxy-siastatin B represented by the general formula (VIII):

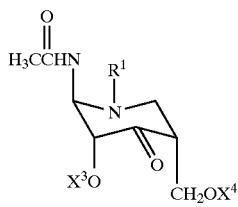

(VIII)

wherein $R^1$, $X^3$ and $X^4$ have the same meanings as above;

reducing the keto group at 4-position of the compound of the formula (VIII), to produce an N-protected or unprotected-4-epi-5-O-protected-3-protected hydroxymethyl-3-decarboxy-siastatin B represented by the general formula (IX):

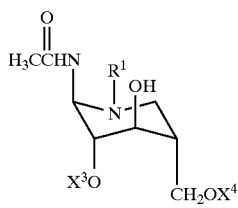

(IX)

wherein $R^1$, $X^3$ and $X^4$ have the same meanings as above;

and then eliminating the imino-protecting group ($R^1$) if present, and eliminating the hydroxyl-protecting groups ($X^3$ and $X^4$) from the compound of the formula (IX).

In carrying out the process according to the fifth aspect of this invention, first of all, an N-protected or unprotected-4,5-O-protected-3-hydroxymethyl-3-decarboxy-siastatin B of the formula (II) is subjected to a hydrolytic reaction in the presence of an acid such as acetic acid and hydrochloric acid or a base such as sodium hydroxide and potassium carbonate in a solvent, or subjected to a hydrogenolytic reaction in the presence of a catalyst such as palladium and Raney nickel in a solvent. Thereby, the hydroxyl-protecting groups ($X^1$ and $X^2$) of the compound of the formula (II) are eliminated to generate the free hydroxyl groups and thus an N-protected or unprotected-3-hydroxymethyl-3-decarboxy-siastatin B of the formula (VI) is produced.

Subsequently, the compound of the formula (VI) is reacted with an alkylsilyl halide such as tert-butyl dimethylsilyl chloride and trimethylsilyl chloride; alkoxyalkyl halide such as methoxyethoxymethyl chloride and methoxymethyl chloride; an alkyl halide and an aralkyl halide; and an acid chloride such as acetyl chloride, in the presence of a base such as imidazole, N,N-diisopropyl-ethylamine, triethylamine and pyridine, in a solvent such as N,N-dimethylformamide, methylene chloride, chloroform and tetrahydrofuran. Thereby, both the hydroxymethyl group at 3-position and the free hydroxyl group at 5-position of the compound of the formula (VI) are protected to produce an N-protected or unprotected-5-O-protected-3-protected hydroxymethyl-3-decarboxy-siastatin B of the formula (VII).

Then, the hydroxyl group at 4-position of the compound of the formula (VII) is oxidized with an oxidizing agent such as ruthenium tetraoxide, pyridinium chloroformate, pyridinium dichromate, manganese dioxide and Dess-Martin Periodinane reagent in a solvent such as methylene chloride, carbon tetrachloride and tetrahydrofuran. Thereby, an N-protected or unprotected-4-keto-5-O-protected-3-protected hydroxymethyl-3-decarboxy-siastatin B is produced. Subsequently, the keto group at 4-position of the compound of the formula (VIII) is reduced by reacting the compound with a metal hydride such as lithium borohydride, sodium borohydride and lithium aluminum hydride, or is reduced by hydrogenation in the presence of a catalyst such as palladium and Raney nickel, in a solvent such as methylene chloride, acetonitrile and tetrahydrofuran. Thereby, an N-protected or unprotected-4-epi-5-O-protected-3-protected hydroxymethyl-3-decarboxy-siastatin B of the formula (IX) is produced. Subsequently, from the compound of the formula (IX), the imino-protecting group ($R^1$), where present, is eliminated by conventional procedures such as an acid or base treatment and hydrogenolysis. Also, the hydroxyl-protecting groups ($X^3$ and $X^4$) are eliminated by conventional procedures such as an acid or base treatment and hydrolysis, to produce the aimed 3-decarboxy-4-epi-3-hydroxymethyl-siastatin B of the formula (V).

Next, the process for producing 6-deacetamido-3-decarboxy-4-epi-3-hydroxymethyl-6-trifluoroacetamido-siastatin B of the formula (X) according to the third aspect of this invention is described below.

In the production of 6-deacetamido-3-decarboxy-4-epi-3-hydroxymethyl-6-trifluoroacetamido-siastatin B of the formula (X), there is used as the starting compound an N-protected or unprotected-4,5-O-protected-6-deacetamido-3-hydroxymethyl-6-trifluoroacetamido-3-decarboxy-siastatin B of the formula (IV) which was obtained as the intermediate in the process according to the fifth aspect of this invention.

The compound of the formula (IV) as described above is used as the starting compound and allowed to be converted chemically in a plural of steps, so that 6-deacetamido-3-decarboxy-4-epi-3-hydroxymethyl-6-trifluoroacetamido-siastatin B of the formula (X) can be produced.

Namely, according to the sixth aspect of this invention, there is provided a process for the production of 6-deacetamido-3-decarboxy-4-epi-3-hydroxymethyl-6-trifluoro-acetamido-siastain B represented by the formula (X):

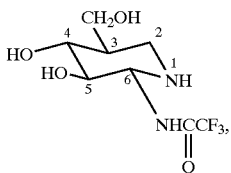

(X)

characterized in that the process comprises:
providing an N-protected or unprotected-4,5-O-protected-6-deacetamido-3-hydroxymethyl-6-trifluoroacetamido-3-decarboxy-siastatin B represented by the general formula (IV):

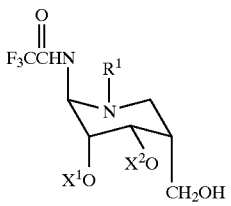

(IV)

wherein $R^1$ is a hydrogen atom or an imino-protecting group, $X^1$ and $X^2$ each are a hydroxyl-protecting group, or both $X^1$ and $X^2$ together denote a divalent hydroxyl-protecting group;

eliminating the hydroxyl-protecting groups ($X^1$ and $X^2$) from the compound of the formula (IV), to produce an N-protected or unprotected-6-deacetamido-3-hydroxymethyl-6-trifluoroacetamido-3-decarboxy-siastatin B represented by the general formula (XI):

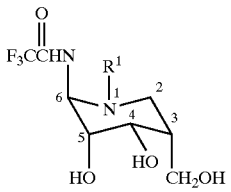

(XI)

wherein $R^1$ has the same meaning as above;

protecting both of the hydroxyl group at 3-position and the free hydroxyl group at 5-position of the compound of the formula (XI), to produce an N-protected or unprotected-5-O-ptotected-6-deacetamido-3-protected hydroxymethyl-6-trifluoroacetamido-3-decarboxy-siastatin B represented by the general formula (XII):

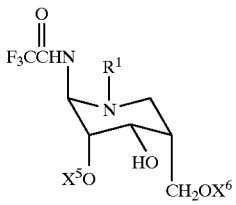

(XII)

wherein $R^1$ is a hydrogen atom or an imino-protecting group, $X^5$ and $X^6$ each are a hydroxyl-protecting group;

oxidizing the hydroxyl group at 4-position of the compound of the formula (XII), to produce an N-protected or unprotected-5-O-ptotected-4-keto-6-deacetamido-3-protected hydroxymethyl-6-trifluoroacetamido-3-decarboxy-siastatin B represented by the general formula (XIII):

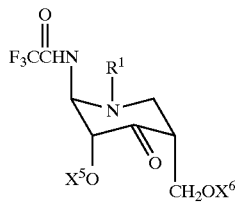

(XIII)

wherein $R^1$, $X^5$ and $X^6$ have the same meanings as above;

reducing the keto group at 4-position of the compound of the formula (XIII), to produce an N-protected or unprotected-5-O-ptotected-4-epi-6-deacetamido-3-protected hydroxymethyl-6-trifluoroacetamido-3-decarboxy-siastatin B represented by the general formula (XIV):

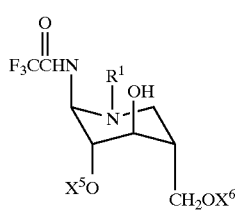

(XIV)

wherein $R^1$, $X^5$ and $X^6$ have the same meanings as above;

and then eliminating the imino-protecting group ($R^1$) if present, and eliminating the hydroxyl-protecting groups ($X^5$ and $X^6$) from the compound of the formula (XIV).

In carrying out the process of the sixth aspect of this invention, the N-protected or unprotected-4,5-O-protected-6-deacetamido-3-hydroxymethyl-3-trifluoroacetamido-3-decarboxy-siastatin B of the formula (IV) is subjected to hydrolytic reaction in the presence of an acid such as acetic acid and hydrochloric acid or a base such as sodium hydroxide and potassium carbonate in a solvent, or is subjected to hydrogenolytic reaction in the presence of a catalyst such as palladium and Raney nickel in a solvent. Thereby, the hydroxyl-protecting groups ($X^1$ and $X^2$) of the compound of the formula (IV) are eliminated to generate the free hydroxyl groups. Thus, the N-protected or unprotected-3-hydroxymethyl-6-trifluoroacetamido-3-decarboxy-siastatin B of the formula (XI) is produced.

The compound of the formula (XI) is then reacted with an alkylsilyl halide such as tert-butyl dimethylsilyl chloride and trimethylsilyl chloride; an alkoxyalkyl halide such as methoxyethoxymethyl chloride and methoxymethyl chloride; an alkyl halide and an aralkyl halide; and acid chloride such as acetyl chloride, in the presence of a base such as imidazole, N,N-diisopropylethylamine, triethylamine and pyridine in a solvent such as N,N-dimethylformamide, methylene chloride, chloroform and tetrahydrofuran. Thereby, both of the hydroxymethyl group at 3-position and the free hydroxyl group at 5-position of the compound of the formula (XI) are protected to produce the N-protected or unprotected -5-O-protected-6-deacetamido-3-protected hydroxymethyl-6-trifluoroacetamido-3-decarboxy-siastatin B of the general formula (XII).

Then, the hydroxyl group at 4-position of the compound of the formula (XII) is oxidized with an oxidizing agent such as ruthenium tetraoxide, pyridinium chloroformate, pyridinium dichromate, manganese dioxide and Dess-Martin Periodinane reagent in a solvent such as methylene chloride, carbon tetrachloride and tetrahydrofuran. Thereby, the N-protected or unprotected-5-O-protected-4-keto-6-deacetamido-3-protected hydroxymethyl-6-trifluoroacetamido-3-decarboxy-siastatin B of the formula (XIII) is produced.

Subsequently, the keto group at 4-position of the compound of the formula (XIII) is reduced by hydrogenation in the presence of a metal halide such as lithium borohydride, sodium borohydride and lithium aluminum hydride or in the presence of a catalyst such as palladium and Raney nickel, in a solvent such as methylene chloride, acetonitrile and tetrahydrofuran. Thereby, the N-protected or unprotected-4-epi-6-deacetamido-3-decarboxy-siastatin siastatin B of the formula (XIV) is produce.

Thereafter, from the compound of the formula (XIV), the imino-protecting group ($R^1$), where present, is eliminated by conventional procedures such as acid or base treatment and hydrolysis. Also, the hydroxyl-protecting groups ($X^5$ and $X^6$) are eliminated by conventional procedures such as acid or base treatment and hydrolysis, to produce 6-deacetamido-3-decarboxy-4-epi-3-hydroxymethyl-6-trifluoroacetamido-siastatin B of the formula (X).

When the compounds of the formulae (I), (V) and (X) obtained in the processes according to the fourth aspect, the fifth aspect and the sixth aspect of this invention are afforded in the form of an acid addition salt such as hydrochloric acid salt, the aqueous solution of the acid addition salt may be treated with a cation-exchange resin, for example, Dow X 50W (a product of Dow Chemical Co., U.S.A) ($H^+$ type) according to conventional procedures, or purified by a chromatography using the solvent containing ammonia, to produce the compounds of the formulae (I), (V) and (X) in the form of the free base.

Furthermore, as will be apparent from Test Examples 1 to 5 as described above, all and each of 6-deacetamido-3-decarboxy-3-hydroxymethyl-6-trifluoroacetamido-siastain B of the formula (I), 3-decarboxy-4-epi-3-hydroxymethyl-siastain B of the formula (V) and 6-deacetamido-3-decarboxy-4-epi-3-hydroxymethyl-6-trifluoroacetamido-siastain B of the formula (X), which are a novel compound according to this invention, has the glycosidase-inhibitory activity. Therefore, every one of these novel siastatin B derivatives, owing to its glycosidase-inhibitory activity, is useful as an inhibitor to the metastasis of cancer cells and also is useful for the therapeutic treatment or prevention of diabetes and obesity. Furthermore, the novel siastatin B derivatives according to this invention may be admixed with a conventional and pharmaceutically acceptable solid or liquid carrier to be formulated into a pharmaceutical composition.

According to the seventh aspect of this invention, therefore, there is provided a pharmaceutical composition comprising as an active ingredient 6-deacetamido-3-decarboxy-3-hydroxymethyl-6-trifluoroacetamido-siastain B of the formula (I), or 3-decarboxy-4-epi-3-hydroxymethyl-siastain B of the formula (V), or 6-deacetamido-3-decarboxy-4-epi-3-hydroxymethyl-6-trifluoroacetamido-siastain B of the formula (X) as described hereinbefore, or a pharmaceutically acceptable salt thereof, in combination with a pharmaceutically acceptable carrier.

The pharmaceutical composition according to the seventh aspect of this invention has a glycosidase-inhibitory activity and thus may be administered as a medicine to animals, including human. Particularly, the pharmaceutical composition according to the seventh aspect of this invention has an effect in the therapeutic treatment of cancers, or the treatment and prevention of diabetes or obesity.

In the pharmaceutical composition according to the seventh aspect of this invention, the carrier to be mixed may be a solid or liquid carrier which is conventionally used in pharmaceutical techniques. The solid carrier may be, for example, starch, lactose, crystalline cellulose or calcium carbonate, and the liquid carrier may be, for example, physiological saline, aqueous ethanol or ethanol. The amount of the novel siastatin B derivative contained as an active ingredient in the composition is not limited, as far as it is sufficient to treat diseases, but it may be, for example, in a range of from not less than 0.01% to less than 100%, preferably from not less than 0.1% to less than 80%, based on the total weight of the composition.

When the pharmaceutical composition according to the seventh aspect of this invention is administered to the patients, it may be formulated according to conventional procedures, depending on various sorts of carriers used, the mode of administration or the medicinal form used. The formulations for oral administration include tablets, pills, granules, capsules, powders, liquids, suspensions, syrups, tongue purgatives, etc. Moreover, the formulations for parenteral administration include injections, percutaneous absorbents, inhalations, suppositories, etc. In the formulation, additives for medicines, such as surface active agents, excipients, stabilizers, wetting agents, disintegrating agents, dissolution auxiliary agents, isotonic agents, buffer agents, colorants and flavors may suitably be incorporated.

The optimal dosage of the novel siastatin B derivative of this invention to be used as a medicine may vary depending on age and body weight of the patients, the type and conditions of diseases, and the route of administration employed. However, when orally administered to human, the dosage may be in the range of 1.0 to 1000 mg/kg per day for one adult. When intravenously administered, the siastatin B derivative may similarly be administered in the range of 1.0 to 100 mg/kg.

Furthermore, according to the eighth aspect of this invention, there is provided a glycosidase inhibitor which consists of 6-deacetamido-3-decarboxy-3-hydroxymethyl-6-trifluoroacetamido-siastatin B of the formula (I), or 3-decarboxy-4-epi-3-hydroxymethyl-siastatin B of the formula (V), or 6-deacetamido-3-decarboxy-4-epi-3-hydroxymethyl-6-trifluoroacetamido-siastatin B of the formula (X) as described above, or a pharmaceutically acceptable salt thereof. In the glycosidase inhibitor according to the eighth aspect of this invention, each of the siastatin B derivatives as described above or a salt thereof can be used alone as it is. The inhibitor can be employed, for example, as a reagent for an enzyme.

Furthermore, according to the ninth aspect of this invention, there is provided use of 6-deacetamido-3-decarboxy-3-hydroxymethyl-6-trifluoroacetamido-siastatin B of the formula (I), or 3-decarboxy-4-epi-3-hydroxymethyl-siastatin B of the formula (V), or 6-deacetamido-3-decarboxy4-epi-3-hydroxymethyl-6-trifluoroacetamido-siastatin B of the formula (X), or its pharmaceutically acceptable salt in the manufacture of a pharmaceutical composition.

Best Mode Carrying Out the Invention

An example of the preparation of N-(tert-butoxycarbonyl)-4,5-O-benzylidene-3-hydroxymethyl-3-decarboxy-siastatin B (Compound IIa), which is one example of the starting compound of the formula (II) used in the process according to the fourth aspect of this invention, is illustrated by Referential Example 1 given below. Moreover, the present inventions are illustrated with reference to Examples 1, 2 and 3 which demonstrate the preparation of the compounds of the formulae (I), (V) and formula (X) according to the third aspect, the fourth aspect and the fifth aspect of this invention.

However, these Examples are given only by way of example of the present invention but are not limitative of this invention. It is needless to mention that various variations and modifications can be made within the scope of this invention.

Referential Example 1

Preparation of N-(tert-butoxycarbonyl)-4,5-O-benzylidene-3-hydroxymethyl-3-decarboxy-siastatin B (Compound IIa)

N-(tert-butoxycarbonyl)-4,5-O-benzylidene-siastatin B (5.60 g and 13.8 mmol), which was prepared by the method of Sato et al. described in the "Carbohydrate Research", 286, 173–178 (1996), was dissolved in N,N-dimethylformamide (DMF)(10 ml), and to the resulting solution were added N,N-diisopropylethylamine (4.80 ml, 27.6 mmol) and 2-methoxyethoxymethyl chloride (3.15 ml and 27.6 mmol). The mixture thus obtained was stirred at room temperature for 12 hours.

The resulting reaction solution was concentrated under reduced pressure and then to the residue was added ethyl acetate. The resultant mixture was washed twice with saturated aqueous sodium chloride solution. The remaining organic layer was dried over anhydrous magnesium sulfate, followed by filtration. After the filtrate was concentrated under reduced pressure, the residue so obtained was purified by a column chromatography on silica gel with using chloroform-methanol (19:1) as a developing solvent, to afford 6.65 g (98%) of the methoxyethoxymethyl ester of N-(tert-butoxycarbonyl)-4,5-O-benzylidene-siastatin B in the form of colorless foam.

Specific rotation: E C] $^{28}{}_D$+22.1° (c 0.91, methanol).

This compound (6.50 g, 13.1 mmol) was dissolved in a mixed solvent of tetrahydrofuran (100 ml) and 2,2,2-trifluoroethanol (10 ml). To the resulting solution was added sodium borohydride (995 mg, 26.3 mmol). The resulting mixture was stirred at room temperature for one hour to perform the reduction reaction. Thereafter, to the reaction solution was added water (30 ml) to stop the reaction. The resultant mixture was further stirred at room temperature for 30 minutes. The resulting reaction solution was concentrated under reduced pressure, and then the residue was added with and then extracted twice with chloroform. The organic layers (the chloroform extracts) are combined, dried over anhydrous magnesium sulfate and then filtered. The filtrate was concentrated under reduced pressure, and then the residue was purified by a column chromatography on silica gel with using chloroform as a developing solvent, to afford 4.87 g (94%) of the titled compound (Compound IIa) in the form of colorless foam.

Specific rotation: $[\alpha]^{27}{}_D$+87.3° (c 0.93, methanol);

$^1$H-NMR spectrum (CDCl$_3$, δ ppm): 1.47(9H, s, COOC (CH$_3$)$_3$), 1.99(3H, s, —NHCOCH$_3$), 2.17(1H, t, J=5.4 Hz, —CH$_2$OH), 2.18–2.30(1H, m, 5-H), 3.31(1H, br t, J=12.5 Hz, 6-Hax), 3.51(1H, dd, J=12.5, 4.2 Hz, 6-Heq), 3.72–3.87 (2H, m, —CH$_2$OH), 4.59(1H, dd, J=7.6, 2.2 Hz, 3-H), 4.63–4.73(1H, m, 4-H), 5.73(1H, s, =CHPh), 5.89(2H, brs, 2-H and —NHCOCH$_3$), 7.34–7.44(5H, m, Ph);

IR spectrum (CHCl$_3$): 3450, 3000, 1680, 1390, 1370, 1170, 1090, 1070 cm$^{-1}$;

Mass spectrum (FAB-MS): m/z 393.3(M+H)$^+$, 337.3, 234.2, 154.1, 136.1, 57.1.

Next, the process according to the fourth aspect of this invention is illustrated by Example given below.

EXAMPLE 1

(1) Preparation of N-(tert-butoxycarbonyl)-4,5-O-benzylidene-6-N-deacetyl-3-hydroxymethyl-3-decarboxy-siastatin B (Compound IIIa)

The compound IIa (3.0 g, 7.64 mmol), which was obtained by the process described in Referential Example 1, was dissolved in hydrazine hydrate (H$_2$NNH$_2$.xH$_2$O, 30 ml). The solution was stirred at 70° C. for seven days. The reaction solution was cooled down to room temperature, followed by concentrating under reduced pressure. The residue was added with water and extracted three times with chloroform. The resulting organic extracts were combined, dried over anhydrous magnesium sulfate and then filtered. The filtrate was concentrated under reduced pressure, and then the residue was purified by a column chromatography on silica gel with using ethyl acetate-methanol (19:1) as a developing solvent, to afford 1.07 g (40%) of the titled compound (Compound IIIa) in the form of colorless foam. At this time, 1.56 g (52%) of the unreacted Compound IIa was recovered.

Specific rotation: $[\alpha]^{28}{}_D$+25.7° (c 0.81, methanol);

$^1$H-NMR spectrum (CDCl$_3$, δ ppm): 1.49(9H, s, COOC (CH$_3$)$_3$), 2.54–2.64(1H, m, 5-H), 3.36(1H, br t, J=12.5 Hz, 6-Hax), 3.48(1H, dd, J=12.2, 5.4 Hz, 6-Heq), 3.79(2H, d, J=5.9 Hz, —CH$_2$OH), 4.36(1H, dd, J=8.1, 1.7 Hz, 3-H), 4.62(1H, dd, J=8.1, 2.7 Hz, 4-H), 5.27(1H, br s, 2-H), 5.74(1H, s, CHPh), 7.26–7.46(5H, m, Ph);

IR spectrum (CHCl$_3$): 3400, 2970, 1685, 1460, 1410, 1370, 1170, 1090, 1070 cm$^{-1}$;

Mass spectrum (FAB-MS): m/z 351.2 (M+H)$^+$, 334.2, 234.2, 154.1, 136.1, 57.1.

(2) Preparation of N-(tert-butoxycarbonyl)-4,5—O—benzylidene-6-deacetamido-3-decarboxy-3-hydroxymethyl-6-trifluoroacetamido-siastatin B (Compound IVa)

Compound IIIa (3.0 g, 8.56 mmol), which was obtained in Example 1, step (1), was dissolved in N,N-dimethylformamide (30 ml), and to the resulting solution were added N,N-diisopropylethylamine (14.8 ml, 85.6 mmol) and ethyl trifluoroacetate (10.2 ml, 85.6 mmol). The resulting mixture was stirred at 60° C. for 15 hours.

The reaction solution was concentrated under reduced pressure, and then the residue was added with ethyl acetate and washed twice with saturated aqueous sodium chloride solution. The organic layer so obtained was dried over anhydrous magnesium sulfate and then filtered. The filtrate was purified by a column chromatography on silica gel with using n-hexane-ethyl acetate (1:1) as a developing solvent, to afford 2.77 g (73%) of the titled compound (Compound IVa) in the form of colorless foam.

specific rotation: $[\alpha]^{28}{}_D$+67.7° (c 0.96, methanol);

$^1$H-NMR spectrum (CDCl$_3$, δ ppm): 1.47(9H, S, COOC (CH$_3$)$_3$), 1.95(1H, t, J=5.4 Hz, —CH$_2$OH), 2.12–2.23(1H, m, 5-H), 3.31(1H, br t, J=12.5 Hz, 6-Hax), 3.59(1H, dd, J=12.2, 3.9 Hz, 6-Heq), 3.77–3.90(2H, m, —CH$_2$OH), 4.62–4.73(2H, m, 3-H and 4-H), 5.76(1H, s, =CHPh), 5.94(1H, br s, 2-H), 6.65(1H, br s, —NHCOCF$_3$), 7.36–7.46 (5H, m, Ph);

IR spectrum (CHCl$_3$): 3440, 2980, 1740, 1705, 1395, 1370, 1165, 1090, 1070 cm$^{-1}$;

Mass spectrum (FAB-MS): m/z 447.2 (M+H)$^+$, 391.1, 234.2, 154.1, 128.1, 57.1.

(3) Preparation of the hydrochloride of 6-deacetamido-3-decarboxy-3-hydroxymethyl-6-trifluoroacetamido-siastatin B of the formula (I)

(i) Compound IVa (2.50 g, 5.60 mmol), which was obtained in Example 1, step (2), was dissolved in methanol (200 ml). To the resulting solution was added 10% palladium on carbon (1.25 g), and then the mixture was stirred under hydrogen atmosphere at room temperature for 16 hours to conduct the reaction for elimination of the benzylidene group. The 10% palladium on carbon was removed from the reaction solution by filtration using celite, and the filtrate was concentrated under reduced pressure. The residue obtained was purified by a column chromatography on silica gel with using chloroform-methanol (19:1) as a developing solvent, to afford 1.85 g (92%) of N-(tert-butoxycarbonyl)-6-deacetamido-3-decarboxy-3-hydroxymethyl-6-trifluoroacetamido-siastatin B (Compound XIa) in the form of colorless foam.

Physicochemical properties of said Compound XIa are as follows:

Specific rotation: $[\alpha]^{28}_D$ +45.7° (c 0.59, methanol);

$^1$H-NMR spectrum (CDCl$_3$, δ ppm): 1.48(9H, S, COOC(CH$_3$)$_3$), 1.87–1.96(1H, m, 5-H), 2.43(1H, t, J=5.4 Hz, —CH$_2$CH), 3.21(1H, d, J=3.4 Hz, 4-OH), 3.29(1H, m, 3-OH), 3.49(1H, dd, J=14.2, 8.8 Hz, 6-Hax), 3.60(1H, dd, J=14.2, 4.4 Hz, 6-Heq), 3.77–3.90(3H, m, —CH$_2$OH and 3-H), 4.29(1H, dd, J=6.8, 3.4 Hz, 4-H), 5.55 (1H, br t, J=8.3 Hz, 2-H);

IR spectrum (CHCl$_3$): 3375, 2980, 1730, 1685, 1540, 1410, 1370, 1250, 1170 cm$^{-1}$;

Mass spectrum (FAB-MS): m/z 359.2 (M+H)$^+$, 307.2, 303.2, 289.2, 154.1, 138.1, 107.1, 57.1.

(ii) Compound XIa (70 mg, 0.195 mmol) thus obtained was dissolved in dichloromethane (1 ml), and to the resulting solution was added a 4N hydrogen chloride-dioxane solution (0.25 ml). Then the resulting mixture was stirred at room temperature for 30 minutes. Whereupon, the N-tert-butoxycarbonyl group was thus eliminated. Diethyl ether was added to the resulting reaction solution containing colorless solids deposited and suspended therein. Solid solution was then fully stirred, and the deposited colorless solids were precipitated by centrifugation and the supernatant was discarded. The resulting precipitates were dried under reduced pressure to afford 41 mg (80%) of the titled compound [the compound of formula (I)] in the form of colorless solid.

Next, the process according to the fifth aspect of this invention is illustrated by Example given below.

EXAMPLE 2

(1) Preparation of N-(tert-butoxycarbonyl)-3-decarboxy-3-hydroxymethyl-siastatin B (Compound VIa)

Compound IIa (1.20 g, 3.06 mols) as obtained by the process described in Referential Example 1 was dissolved in methanol (120 ml), and to the resulting solution was added 10% palladium on carbon (500 mg). Then, the resulting mixture was stirred under hydrogen atmosphere at room temperature for 6 hours to conduct the reaction for elimination of the benzylidene group. After 10% palladium on carbon was removed by filtration using celite, the filtrate was concentrated under reduced pressure. The residue was purified by a column chromatography on silica gel with using chloroform-methanol (3:2) as a developing solvent, to afford 877 mg (94%) of the titled compound (compound VIa) in the form of a colorless foam.

Specific rotation: $[\alpha]^{25}_D$ +50.50 (c 0.49, methanol);

Colorless needle crystals as recrystallized from ethanol-ethyl ether showed a melting point (decomposition) of 201–202° C.;

$^1$H-NMR spectrum (CDCl$_3$, δ ppm): 1.45(9H, s, COOC(CH$_3$)$_3$), 1.91–1.98(1H, m, 5-H), 1.96(3H, s, —NHCOCH$_3$), 3.10(1H, dd, J=14.2, 3.4 Hz, 6-Hax), 3.71(1H, dd, J=5.4, 2.4 Hz, 3-H), 3.73(1H, dd, J=11.2, 8.1 Hz, —CH$_2$OH), 3.80(1H, dd, J=11.2, 3.9 Hz, —CH$_2$OH), 3.99(1H, dd, J=5.4, 3.2 Hz, 4-H), 4.14(1H, d, with a small coupling, J=14.2 Hz, 6-Heq), 5.99(1H, d, J=2.4 Hz, 2-H);

IR spectrum (KBr): 3290, 2980, 2920, 1710, 1670, 1650, 1540, 1430, 1270, 1160, 1100, 1010, 960 cm$^{-1}$;

Mass spectrum (FAB-MS): m/z 305.3(M+H)$^+$, 289.2, 249.2, 154.1, 146.2, 136.1, 107.1, 57.1.

(2) Preparation of N-(tert-butoxycarbonyl)-5-O-(tert-butyldimethylsilyl)-3-(tert-butyldimethylsilyloxy)methyl-3-decarboxy-siastatin B (Compound VIIa)

Compound VIa (2.20 g, 7.23 mmol) obtained in the above step (1) was dissolved in N,N-dimethylformamide (DMF) (30 ml). To the resulting solution were added imidazole (3.44 g, 50.6 mmol) and tert-butyldimethylsilyl chloride (3.81 g, 25.3 mmol), and the mixture so obtained was stirred at room temperature for 16 hours. The resulting reaction solution was concentrated under reduced pressure, and then the residue was added with ethyl acetate and washed twice with saturated aqueous sodium chloride solution. The organic solution as formed was dried over anhydrous magnesium sulfate and then filtered. After the filtrate was concentrated under reduced pressure, the resulting residue was purified by a column chromatography on silica gel with using n-hexane-ethyl acetate as a developing solvent, to afford 1.89 g (49%) of the titled compound (Compound VIIa) in the form of a colorless oil.

Specific rotation: $[\alpha]^{23}_D$ +37.3° (c 1.03, methanol);

$^1$H-NMR spectrum (CDCl$_3$, δ ppm): 0.05, 0.10 and 0.14 (6H, 3H and 3H, each s, (CH$_3$)$_2$ of t-butyldimethylsilyl), 0.89 and 0.94 (each 9H, each s, (CH$_3$)$_3$ of t-butyldimethylsilyl), 1.46(9H, s, COOC(CH$_3$)$_3$), 1.73–1.82 (1H, m, 5-H), 2.04(1H, s, NHCOCH$_3$), 2.76(1H, d, J=6.8 Hz, —OH), 3.28–3.37(1H, m, 6-Hax), 3.52–3.63(4H, m, —CH$_2$OTBDMS, 3-H and 6-H), 4.14(1H, br t, J=2.9 Hz, 4-H), 5.58(1H, br t, J=8.1 Hz, 2-H), 7.40(1H, br s, —NH);

IR spectrum (CHCl$_3$): 3400, 2950, 2930, 2860, 1680, 1500, 1470, 1410, 1380, 1260, 1160, 1100, 840 cm$^{-1}$;

Mass spectrum (FAB-MS): m/z 533.3 (M+H)$^+$, 474.3, 374.3, 316.2, 242.2, 171.2, 73.1, 57.1.

(3) Preparation of N-(tert-butoxycarbonyl)-5-O-(tert-butyldimethylsilyl)-3-(tert-butyldimethylsilyloxy)methyl-3-decarboxy-4-keto-siastatin B (Compound VIIIa)

Compound VIIa (640 mg, 1.20 mmol) obtained in the above step (2) was dissolved in anhydrous dichloromethane (30 ml). To the resulting solution was added the Dess-Martin oxidizing reagent (764 mg, 1.80 mmol) which was prepared according to the method described in the literature (J. Am. Chem. Soc., 1991, 113, 7277–7287; J. Org. Chem., 1993, 58, 2899). The resultant mixture was stirred at room temperature for 2 hours. The resulting reaction solution was diluted with chloroform, neutralized with saturated aqueous sodium hydrogen carbonate solution and then separated into two layers. The so separated organic layer was washed with water, dried over anhydrous magnesium sulfate and then filtered. After the filtrate was concentrated under reduced pressure, the residue so obtained was purified by a column chromatography on silica gel with using n-hexane-ethyl acetate (3:1) as a developing solvent, to afford 628 mg (98%) of the titled compound (Compound VIIIa) in the form of a colorless foam.

Specific rotation: $[\alpha]^{28}_D$+45.0° (c 0.84, methanol);

$^1$H-NMR spectrum (CDCl$_3$, δ ppm): 0.06, 0.07 and 0.10 (6H, 3H, and 3H, each s, (CH$_3$)$_2$ of t-butyldimethylsilyl), 0.88 and 0.89 (each 9H, each s, (CH$_3$)$_3$ of t-butyldimethylsilyl), 1.47(9H, s, COOC(CH$_3$)$_3$), 1.98(3H, s, NHCOCH$_3$), 2.53–2.62(1H, m, 5-H), 3.62(1H, br t, J=9.8 Hz, 6-Hax), 3.97(2H, m, 6-Heq and —CH$_2$OTBDMS), 4.08(1H, dd, J=13.7, 4.9 Hz, —CH$_2$OTBDMS), 4.73(1H, br s with a small coupling, 3-H), 5.14(1H, br s, 2-H), 6.31(1H, br s, —NH);

IR spectrum (CDCl$_3$): 3430, 2950, 2930, 2860, 1740, 1680, 1480, 1410, 1260, 1160, 1100, 840 cm$^{-1}$;

Mass spectrum (FAB-MS): m/z 531.4 (M+H)$^+$, 472.3, 416.3, 372.3, 358.2, 314.3, 186.2, 73.1, 57.1.

(4) Preparation of N-(tert-butoxycarbonyl)-5-O-(tert-butyldimethylsilyl)-3-(tert-butyldimethylsilyloxy)methyl-3-decarboxy-4-epi-siastatin B (Compound IXa)

Compound VIIIa (106 mg, 0.20 mmol) obtained in the above step (3) was dissolved in anhydrous acetonitrile (5 ml). To the resulting solution, lithium borohydride (8.7 mg, 0.40 mmol) was added at –50° C., and the resultant mixture was stirred for 30 minutes. A saturated aqueous ammonium chloride solution was added to the resulting reaction solution to stop the reaction, and subsequently the reaction solution was diluted with 20 ml of chloroform and separated into two layers. The so separated organic layer was washed with water, and then dried over anhydrous magnesium sulfate and filtered. After the filtrate was concentrated under reduced pressure, the residue obtained was purified by a column chromatography on silica gel with using n-hexane-ethyl acetate (5:3) as a developing solvent, to afford 79 mg (74%) of the titled compound (Compound IXa) in the form of a colorless foam.

Specific rotation: $[\alpha]^{26}_D$+24.2° (c 0.73, methanol);

$^1$H-NMR spectrum (CDCl$_3$, δ ppm): 0.05, 0.06, 0.10 and 0.14 (each 3H, each s, (CH$_3$)$_2$ of t-butyldimethylsilyl), 0.89(18H, s, (CH$_3$)$_2$ of t-butyldimethylsilyl), 1.47(9H, s, and COOC(CH$_3$)$_3$), 1.78–1.87(1H, m, 5-H), 1.97(3H, s, —NHCOCH$_3$), 2.22(1H, d, J=2.4 Hz, —OH), 3.41(1H, br d, J=13.2 Hz, 6-H), 3.58–3.69(1H, m, 6-H), 3.61(1H, dd, J=10.3, 5.4 Hz, —CH$_2$OTBS), 3.69(1H, br t, J=4.2 Hz, 3-H), 3.75(2H, m, —CH$_2$OTBS and 4-H), 5.74 (1H, br s, 2-H), 7.07(1H, d, J=8.3 Hz, —NH);

IR spectrum (CHCl$_3$): 3400, 2960, 2940, 2860, 1680, 1510, 1470, 1370, 1260, 1100, 840 cm$^{-1}$;

Mass spectrum (FAB-MS): m/z 533.5(M+H)$^+$, 477.4, 374.3, 316.3, 186.2, 73.1, 57.1.

(5) Preparation of the hydrochloride of 3-decarboxy-4-epi-3-hydroxymethyl-siastatin B of the formula (V)

Compound IXa (20 mg, 0.0375 mmol) obtained in the above step (4) was dissolved in anhydrous dioxane (1 ml). To the resulting solution was added a 4N hydrogen chloride-dioxane solution (0.2 ml), and the resultant mixture was stirred at room temperature for 2 hours. To the resulting reaction solution containing colorless solids deposited and suspended therein was added diethyl ether. The resultant mixture was thoroughly stirred, and thereafter the deposited colorless solids were made to precipitate by centrifugation, and the supernatant was discarded. The precipitates thus obtained were dried under reduced pressure to afford 7.2 mg (80%) of the titled compound [the compound of the formula (V)] in the form of a colorless solid.

Next, the process according to the sixth aspect of this invention is illustrated by Example given below.

EXAMPLE 3

(1) Preparation of N-(tert-butoxycarbonyl)-5-O-(tert butyldimethylsilyl)-3-(tert-butyldimethylsilyloxy)methyl-6-deacetamido-3-decarboxy-6-trifluoroacetamido-siastatin B (Compound XIIa)

Compound XIa, which was obtained as an intermediate compound in Example 1, step (3)(i) hereinbefore and was namely N-(tert-butoxycarbonyl)-6-deacetamido-3-decarboxy-3-hydroxymethyl-6-trifluoroacetamido-siastatin B (1.30 g, 3.63 mmol), was dissolved in N,N-dimethylformamide (DMF)(25 ml). To the resulting solution were added imidazole (1.73 g, 25.4 mmol) and tert-butyldimethylsilyl chloride (1.91 g, 12.7 mmol), and the resultant mixture was stirred at room temperature for 16 hours (for O-silylation reaction). The resulting reaction solution was concentrated under reduced pressure, and then the residue obtained was added with ethyl acetate and then washed twice with saturated aqueous sodium chloride solution. The organic solution as formed was dried over anhydrous magnesium sulfate and then filtered. The filtrate was concentrated under reduced pressure-, and the resulting residue was purified by a column chromatography on silica gel with using n-hexane-ethyl acetate (9:1) as a developing solvent, to afford 1.23 g (58%) of the titled compound (compound XIIa) in the form of colorless needle crystals.

Specific rotation: $[\alpha]^{28}_D$+42.5° (c 0.96, methanol);

Melting point: 88–90° C.;

$^1$H-NMR spectrum (CDCl$_3$, δ ppm): 0.06, 0.11 and 0.12 (6H, 3H and 3H, each s, (CH$_3$)$_2$ of t-butyldimethylsilyl), 0.89 and 0.90 (each 9H, each s, (CH$_3$)$_3$ of t-butyldimethylsilyl), 1.47(9H, 5, COOC(CH$_3$)$_3$), 1.83–1.93 (1H, m, 5-H), 2.69(1H, br s, —OH), 3.20(1H, br t, J=13.7 Hz, 6-Hax), 3.63(1H, dd, J=10.3, 7.8 Hz, —CH$_2$TBDMS), 3.69(1H, dd, J=13.7, 3.9 Hz, 6-Heq), 3.75–3.82(2H, m, —CH$_2$TBDMS and 3-H), 3.98(1H, br d, J=2.4 Hz, 4-H), 5.47(1H, br t, J=8.8 Hz, 2-H);

IR spectrum (CHCl$_3$): 3560, 3350, 2950, 2930, 2860, 1730, 1680, 1530, 1460, 1410, 1370, 1250, 1160, 1090, 950, 840 cm$^{-1}$;

Mass spectrum (FAB-MS): m/z 587.4(M+H)$^+$, 531.4, 487.4, 473.3, 374.4, 316.3, 242.3, 186.2, 73.1, 57.1

(2) Preparation of N-(tert-butoxycarbonyl)-5-O-(tert-butyldimethylsilyl)-3-(tert-butyldimethylsilyloxy)methyl-6-deacetamido-3-decarboxy-4-keto-siastatin B (Compound XIIIa)

Compound XIIa (190 mg, 0.324 mmol) obtained in the above step (1) was dissolved in anhydrous dichloromethane (10 ml). To the resulting solution was added the Des-Martin oxidizing reagent (275 mg, 0.648 mmol), and the resultant mixture was stirred at room temperature for 1 hour (for the oxidation reaction of the hydroxyl group at 4-position). The reaction solution obtained was diluted with chloroform, neutralized with saturated sodium hydrogen carbonate solution and then separated into two layers. The so separated organic layer was washed with water, and then dried over anhydrous magnesium sulfate and filtered. The resulting filtrate was concentrated under reduced pressure, and the residue was purified by a column chromatography on silica gel with using n-hexane-ethyl acetate (7:1) as a developing solvent, to afford 183 mg (97%) of the titled compound (Compound XIIIa) in the form of colorless needle crystals.

Specific rotation: $[\alpha]^{27}_D$+23.3° (c 0.70, methanol);

Melting point: 165–167° C.;

$^1$H-NMR spectrum (CDCl$_3$, δ ppm):0.03, 0.06 and 0.12 (3H, 6H and 3H, each s, (CH$_3$)$_2$ of t-butyldimethylsilyl), 0.89(18H, s, (CH$_3$)$_3$ of t-butyldimethylsilyl), 1.47(9H, s, COOC(CH$_3$)$_3$), 2.55–2.63(1H, m, 5-H), 3.63(1H, dd, J=10.3, 9.3 Hz, 6-Hax), 3.99(2H, m, —CH$_2$OTBDMS and 6-Heq), 4.11(1H, dd, J=14.2, 4.9 Hz, —CH$_2$OTBDMS), 4.74(1H, d, J=7.8 Hz, 3-H), 5.17(1H, br t, J=7.1 Hz, 2-H), 7.30(1H, br s, —NH);

IR spectrum (CHCl$_3$): 3420, 2950, 2930, 2860, 1730, 1700, 1470, 1390, 1260, 1170, 1000, 840 cm$^{-1}$;

Mass spectrum (FAB-MS): m/z 585.5 (M+H)$^+$, 529.4, 471.4, 414.4, 372.4, 358.3, 314.3, 284.3, 226.2, 154.2, 73.1, 57.1.

(3) Preparation of N-(tert-butoxycarbonyl)-5-O-(tert-butyldimethylsilyl)-3-(tert-butyldimethylsilyloxy)methyl-6-deacetamido-3-decarboxy-4-epi-6-trifluoroacetamido-siastatin B (Compound XIVa)

Compound XIIIa (110 mg, 0.188 mmol) obtained in the above step (2) was dissolved in anhydrous acetonitrile (3 ml). To the resulting solution, lithium borohydride (8.2 mg, 0.376 mmol) was added at −50° C., and the resultant mixture was stirred for one hour (for the reduction reaction of 4-keto group). An saturated aqueous ammonium chloride solution was added to the resulting reaction solution to stop the reaction, and then the reaction solution was diluted with 30 ml of chloroform and separated into two layers. The organic layer so separated was washed with water, and then dried over anhydrous magnesium sulfate and filtered. The resultant filtrate was concentrated under reduced pressure, and the residue was purified by a column chromatography on silica gel with using n-hexane-ethyl acetate (10:1) as a developing solvent, to afford 96.9 mg (88%) of (Compound XIVa) in the form of a colorless foam.

Specific rotation: $[\alpha]^{25}_D$+20.00 (c 1.02, methanol);

$^1$H-NMR spectrum (CDCl$_3$, δ ppm): 0.04, 0.06, 0.10 and 0.14(each 3H, each s, (CH$_3$)$_2$ of t-butyldimethylsilyl), 0.896 and 0.899(each 9H, each s, (CH$_3$)$_3$ of t-butyldimethylsilyl), 1.47(9H, s, COOC(CH$_3$)$_3$), 1.83–1.93(1H, m, 5-H), 2.25 (1H, d, J=2.9 Hz, —OH), 3.31(1 h, br d, J=11.7 Hz, 6-H), 3.59(1H, dd, J=10.0, 5.1 Hz, —CH$_2$OTBDMS), 3.70–3.81 (4H, m, —CH$_2$OTBDMS, 3-H, 4-H and 6-H), 5.88(1H, br s, 2-H), 8.11(1H, d, J=7.3 Hz, —NH);

IR spectrum (CHCl$_3$): 3370, 2960, 2940, 2870, 1740, 1690, 1540, 1480, 1370, 1260, 1160, 1100, 840 cm$^{-1}$;

Mass spectrum (FAB-MS): m/z 587.5 (M+H)$^+$, 531.5, 487.4, 473.3, 374.4, 316.3, 242.3, 155.2, 73.1, 57.1.

(4) Preparation of 6-deacetamido-3-decarboxy-4-epi-3-hydroxymethyl-6-trifluoroacetamido-siastatin B of the formula (X)

Compound XIVa (40 mg, 0.0682 mmol) obtained in the above step (3) was dissolved in anhydrous dioxane (2 ml). To the resulting solution was added a 4N hydrogen chloride-dioxane solution (0.4 ml), and the resultant mixture was stirred at room temperature for 5 hours. To the resulting reaction solution was added further a 4N hydrogen chloride-dioxane solution (0.6 ml). The mixture so obtained was stirred at room temperature for 14 hours (for the elimination of the imino-protecting group and the hydroxyl-protecting group). To the resulting reaction solution containing colorless solids deposited and suspended therein was added diethyl ether. The resultant mixture was fully stirred, and thereafter the deposited colorless solids were allowed to precipitate by centrifugation and the supernatant was discarded. The precipitates thus obtained were dried under reduced pressure to afford 18.2 mg (91%) of the titled compound, i.e., the compound of the formula (X) in the form of a colorless solid.

Specific rotation: $[\alpha]^{26}_D$+35.0° (c 0.50, methanol);

$^1$H-NMR spectrum (CD$_3$OD, 40° C., δ ppm): 1.88–2.00 (1H, m, 5-H), and 3.11 (1H, br t, J=13.2 Hz, 6-Hax), 3.42 (1H, dd, J=13.2, 4.4 Hz, 6-Heq), 3.51(1H, dd, J=10.3, 9.3 Hz, 4-H), 3.67(1H, dd, J=11.2, 6.4 Hz, —CH$_2$OH), 3.73(1H, dd, J=10.3, 8.8 Hz, 3-H), 3.84(1H, dd, J=11.2, 3.9 Hz, —CH$_2$OH), 4.84(1H, d, J=9.8 Hz, 2-H);

IR spectrum (KBr): 3350, 1740, 1570, 1420, 1230, 1180, 1100, 1060, 990, 880 cm$^{-1}$;

Mass spectrum (FAB-MS): m/z 259.1 (M+H)$^+$, 202.2, 154.1, 146.1, 136.1, 128.1, 107, 77.1, 57.1.

INDUSTRIAL APPLICABILITY

As be apparent from the foregoing descriptions, 6-deacetamido-3-decarboxy-3-hydroxymethyl-6-trifluoroacetamido-siastatin B of the formula (I), 3-decarboxy-4-epi-3-hydroxy-siastatin B of the formula (V) and 6-deacetamido-3-decarboxy-4-epi-3-hydroxymethyl-6-trifluoroacetamido-siastatin B of the formula (X) are provided by the novel processes of this invention.

These novel compounds of this invention have a potent enzyme-inhibitory activity against glycosidase, especially N-acetylgalactosaminidase, galactosidase, glucosidase and mannosidase, and therefore they are useful as medicines for various applications.

What is claimed is:

1. 6-Deacetamido-3-decarboxy-3-hydroxymethyl-6-trifluoroacetamido-siastatin B represented by the formula (I):

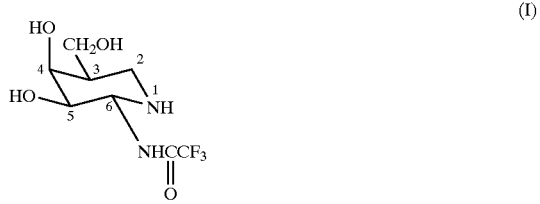

or a pharmaceutically acceptable salt thereof.

2. 3-Decarboxy-4-epi-3-hydroxymethyl-siastatin B represented by the formula (V):

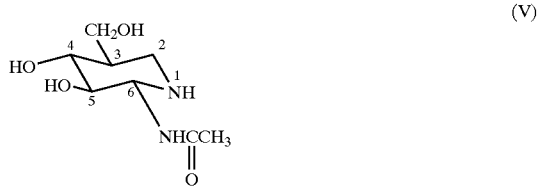

or a pharmaceutically acceptable salt thereof.

3. 6-Deacetamido-3-decarboxy-4-epi-3-hydroxymethyl-6-trifluoroacetamido-siastatin B represented by the formula (X):

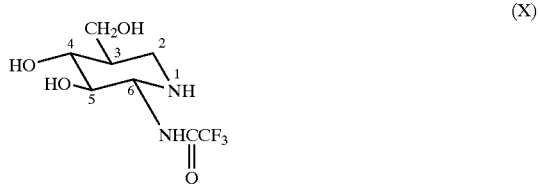

or a pharmaceutically acceptable salt thereof.

4. A process for the production of 6-deacetamido-3-decarboxy-3-hydroxymethyl-6-trifluoroacetamido-siastatin B represented by the formula (I):

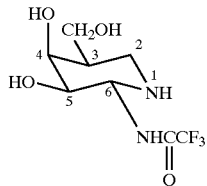

(I)

according to claim 1, characterized in that the process comprises:
eliminating the N-acetyl group from an N-protected or unprotected-4,5-O-protected-3-hydroxymethyl-3-decarboxy-siastatin B represented by the general formula (II):

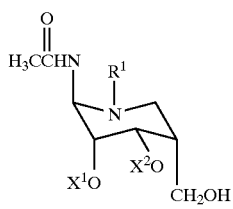

(II)

wherein $R^1$ is a hydrogen atom or an imino-protecting group, $X^1$ and $X^2$ each are a monovalent hydroxyl-protecting group, or both $X^1$ and $X^2$ together denote a divalent hydroxyl-protecting group, to produce an N-protected or unprotected-4,5-O-protected-3-hydroxymethyl-de-N-acetyl-3-decarboxy-siastatin B represented by the general formula (III):

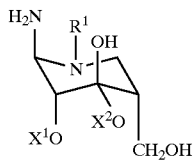

(III)

wherein $R^1$, $X^1$ and $X^2$ have the same meanings as above;
trifluoroacetylating the free amino group of the compound of the formula (III), to produce an N-protected or unprotected-4,5-O-protected-6-deacetamido-3-hydroxymethyl-6-trifluoroacetamido-3-decarboxy-siastatin B represented by the general formula (IV):

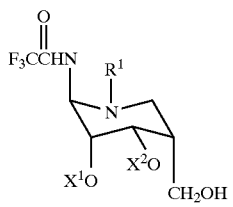

(IV)

wherein $R^1$, $X^1$ and $X^2$ have the same meanings as above; and then eliminating the imino-protecting group ($R^1$) if present, and eliminating the hydroxyl-protecting groups ($X^1$ and $X^2$) from the compound of the formula (IV).

5. A process for the production of 3-decarboxy-4-epi-3-hydroxymethyl-siastatin B represented by the formula (V):

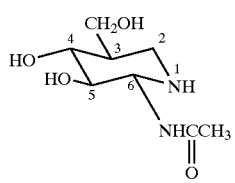

(V)

according to claim 2, characterized in that the process comprises:
eliminating the hydroxyl-protecting groups ($X^1$ and $X^2$) from an N-protected or unprotected-4,5-O-protected-3-hydroxymethyl-3-decarboxy-siastatin B represented by the general formula (II):

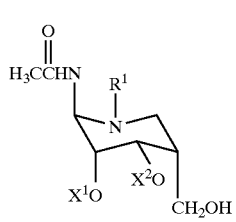

(II)

wherein $R_1$ is a hydrogen atom or an imino-protecting group, and $X^1$ and $X^2$ each are a monovalent hydroxyl-protecting group, or both $X^1$ and $X^2$ together denote a divalent hydroxyl-protecting group, to produce an N-protected or unprotected-3-hydroxymethyl-3-decarboxy-siastatin B represented by the general formula (VI):

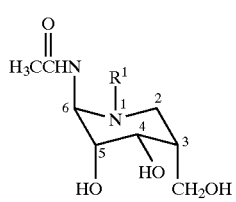

(VI)

wherein $R^1$ has the same meanings as above;
protecting both of the hydroxyl group at 3-position and the free hydroxyl group at 5-position of the compound of the formula (VI), to produce an N-protected or unprotected-5-O-protected-3-protected-hydroxymethyl-3-decarboxy-siastatin B represented by the general formula (VII):

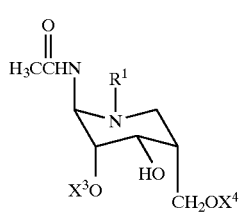

(VII)

wherein $R^1$ is a hydrogen atom or an imino-protecting group, $X^3$ and $X^4$ each denote a hydroxyl-protecting group;
oxidizing the hydroxyl group at 4-position of the compound of the formula (VII), to produce an N-protected or unprotected-4-keto-5-O-protected-3-protected-hydroxymethyl-3-decarboxy-siastatin B represented by the general formula (VIII):

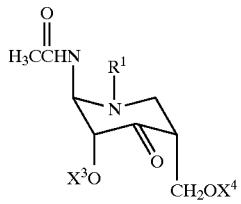
(VIII)

wherein $R^1$, $X^3$ and $X^4$ have the same meanings as above;

reducing the keto group at 4-position of the compound of the formula (VIII), to produce an N-protected or unprotected-4-epi-5-O-protected-3-protected-hydroxymethyl-3-decarboxy-siastatin B represented by the general formula (IX):

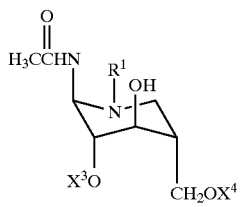
(IX)

wherein $R^1$, $X^3$ and $X^4$ have the same meanings as above;

and then eliminating the imino-protecting group ($R^1$) if present, and eliminating the hydroxyl-protecting groups ($X^3$ and $X^4$) from the compound of the formula (IX).

6. A process for the production of 6-deacetamido-3-decarboxy4-epi-3-hydroxymethyl-6-trifluoroacetamido-siastatin B represented by the formula (X):

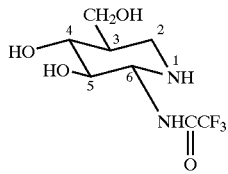
(X)

according to claim 3, characterized in that the process comprises:

providing by the process according to claim 4, an N-protected or unprotected-4,5-O-protected-6-deacetamido-3-hydroxymethyl-6-trifluoroacetamido-3-decarboxy-siastatin B represented by the general formula (IV):

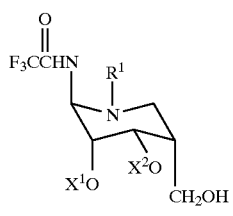
(IV)

wherein $R^1$ is a hydrogen atom or an imino-protecting group, $X^1$ and $X^2$ each are a hydroxyl-protecting group, or both $X^1$ and $X^2$ together denote a divalent hydroxyl-protecting group;

eliminating the hydroxyl-protecting groups ($X^1$ and $X^2$) from the compound of the formula (IV), to produce an N-protected or unprotected-6-deacetamido-3-hydroxymethyl-6-trifluoroacetamido-3-decarboxy-siastatin B represented by the general formula (XI):

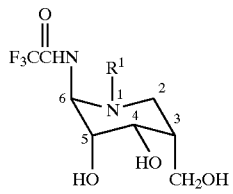
(XI)

wherein $R^1$ has the same meaning as above;

protecting both of the hydroxyl group at 3-position and the free hydroxyl group at 5-position of the compound of the formula (XI), to produce an N-protected or unprotected-5-O-ptotected-6-deacetamido-3-protected hydroxymethyl-6-trifluoroacetamido-3-decarboxy-siastatin B represented by the general formula (XII):

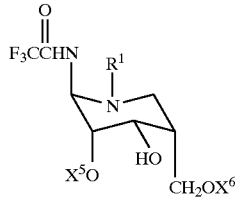
(XII)

wherein $R^1$ is a hydrogen atom or an imino-protecting group, $X^5$ and $x^6$ each are a hydroxyl-protecting group;

oxidizing the hydroxyl group at 4-position of the compound of the formula (XII), to produce an N-protected or unprotected-5-O-ptotected-4-keto-6-deacetamido-3-protected hydroxymethyl-6-trifluoroacetamido-3-decarboxy-siastatin B represented by the general formula (XIII):

(XIII)

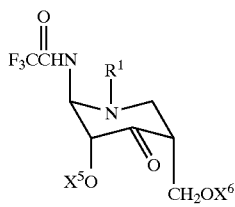

wherein $R^1$, $X^5$ and $X^6$ have the same meanings as above;
reducing the keto group at 4-position of the compound of the formula (XIII), to produce an N-protected or unprotected-5-O-ptotected-4-epi-6-deacetamido-3-protected-hydroxymethyl-6-trifluoroacetamido-3-decarboxy-siastatin B represented by the general formula (XIV):

(XIV)

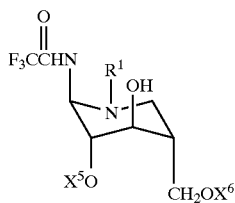

wherein $R^1$, $X^5$ and $X^6$ have the same meanings as above;

and then eliminating the imino-protecting group ($R^1$) if present, and eliminating the hydroxyl-protecting groups ($X^5$ and $X^6$) from the compound of the formula (XIV).

7. A pharmaceutical composition comprising as an active ingredient 6-deacetamido-3-decarboxy-3-hydroxymethyl-6-trifluoroacetamido-siastatin B of the formula (I) as claimed in claim 1, or 3-decarboxy-4-epi-3-hydroxymethyl-siastatin B of the formula (V) as claimed in claim 2, or 6-deacetamido-3-decarboxy-4-epi-3-hydroxymethyl-6-trifluoroacetamido-siastatin B of the formula (X) as claimed in claim 3, or a pharmaceutically acceptable salt thereof, in combination with a pharmaceutically acceptable carrier.

8. A glycosidase inhibitor consisting of 6-deacetamido-3-decarboxy-3-hydroxymethyl-6-trifluoroacetamido-siastain B of the formula (I) as claimed in claim 1, or 3-decarboxy-4-epi-3-hydroxymethyl-siastatin B of the formula (V) as claimed in claim 2, or 6-deacetamido-3-decarboxy-4-epi-3-hydroxymethyl-6-trifluoroacetamido-siastatin B of by the formula (X) as claimed in claim 3, or a pharmaceutically acceptable salt thereof.

* * * * *